(12) United States Patent
Lourdusamy et al.

(10) Patent No.: US 9,315,540 B2
(45) Date of Patent: Apr. 19, 2016

(54) PROCESS FOR THE PREPARATION OF FULVESTRANT

(71) Applicant: INTAS PHARMACEUTICALS LIMITED, Ahmedabad, Gujarat (IN)

(72) Inventors: Mettilda Lourdusamy, Quebec (CA); Ioan Iosif Radu, Quebec (CA); Brijesh Dinkarrai Desai, Gujarat (IN); Pramod Bhagvanjibhai Pansuriya, Gujarat (IN); Sanjay Jagdish Desai, Gujarat (IN)

(73) Assignee: INTAS PHARMACEUTICALS LTD., Ahmedabad (IN)

( * ) Notice: Subject to any disclaimer, the term of this patent is extended or adjusted under 35 U.S.C. 154(b) by 0 days.

(21) Appl. No.: 14/437,533

(22) PCT Filed: Oct. 11, 2013

(86) PCT No.: PCT/IN2013/000616
§ 371 (c)(1),
(2) Date: Apr. 22, 2015

(87) PCT Pub. No.: WO2014/064712
PCT Pub. Date: May 1, 2014

(65) Prior Publication Data
US 2015/0291652 A1    Oct. 15, 2015

(30) Foreign Application Priority Data

Oct. 22, 2012    (IN) .......................... 3083/MUM/2012

(51) Int. Cl.
*C07J 31/00*    (2006.01)
(52) U.S. Cl.
CPC .................... *C07J 31/006* (2013.01)

(58) Field of Classification Search
CPC ............ C07J 75/00; C07J 1/007; C07J 31/006
See application file for complete search history.

(56) References Cited

FOREIGN PATENT DOCUMENTS

| IT | WO 2009/013310 A2 * | 1/2009 |
| WO | 2009/013310 | 1/2009 |
| WO | 2012/129324 | 9/2012 |

OTHER PUBLICATIONS

Greene, Protective Groups in Organic Chemistry, 1981, Jon Wiley & Sons, Inc., New York, pp. 16, 17, 21, 22, 26.*
Zaragoza Dorwald, Side Reactions in Organic Synthesis, 2005, Wiley-VCH Verlag GmbH & Co. KGaA, Weinheim, Preface. p. IX.*
International Search Report corresponding to International Patent Application No. PCT/IN2013/000616, mailed Apr. 18, 2014.

* cited by examiner

*Primary Examiner* — Paul A Zucker
(74) *Attorney, Agent, or Firm* — McAndrews Held & Malloy, Ltd.

(57) ABSTRACT

The present invention relates to an improved process for the preparation of Fulvestrant (I). Also, provided is novel intermediate of Fulvestrant and a process for the preparation of the same.

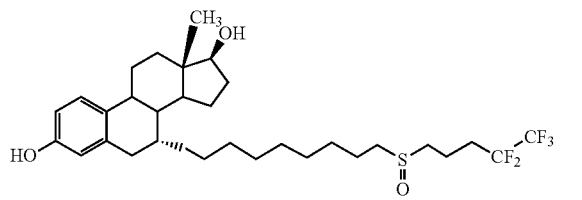

(I)

17 Claims, 2 Drawing Sheets

PROCESS FOR THE PREPARATION OF FULVESTRANT

This application is a national phase filing and claims the priority of international Patent Application No. PCT/IN2013/000616, having an International filing date of Oct. 11, 2013, which claims priority to Indian Patent Application No. 3083/MUM/2012, having a filing date of Oct. 22, 2012. Each of the preceding applications is hereby incorporated by reference in its entirety.

FIELD OF THE INVENTION

The present invention relates to a process for preparation of Fulvestrant (I). Also, provided is novel intermediate of Fulvestrant and a process for the preparation of the same.

BACKGROUND OF THE INVENTION

The present invention relates to processes for making fulvestrant and intermediates useful in the preparation. Fulvestrant is the generic name for (7α,17β)-7-{9-[(4,4,5,5,5-pentafluoropentyl)sulfinyl]nonyl}estra-1,3,5(10)-triene-3,17-diol having the following formula (I)

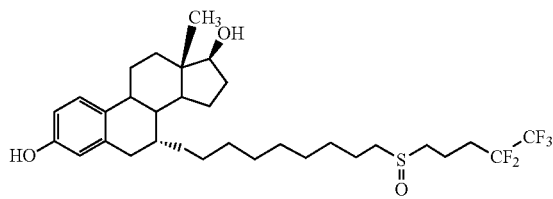

(I)

and was first disclosed in EP 0138504.

Fulvestrant is used to treat locally advanced or metastatic breast cancer in women who have been through menopause. In US, it is sold under brand name FESLODEX.

There are several references reporting the preparation of Fulvestrant, for example WO 2002/32922, WO 2005/077963, Synthesis December 1995, pages 1493-1495, WO 2005/077968, WO 2006/015081, WO 2009/013310 and WO 2010/043404.

The above given references provide a general process for the preparation of Fulvestrant which is summarized in FIG. 1, wherein, R is a protecting group.

The process depicted in FIG. 1 can be described as follows:
The hydroxyl groups at C-3 and C-17 of Estradiol (compound 1) are protected to give compound 2.
Compound 2 is deprotonated and the resulting anion is converted to compound 3 (mixture of 6α and 6β epimers in 4:1 ratio).
Compound 3 is oxidized to obtain compound 4.
Compound 4 is alkylated to compound 5 and deprotected to obtain a compound 6.
Compound 6 is further oxidized to give Fulvestrant.

The oxidation of 6-OH group of compound 3 is very important to get higher industrial yield. All prior disclosed processes mentioned above provide very low yield of compound 4 and hence overall yield of Fulvestrant is reduced. For example, use of aqueous Sodium hypochlorite as oxidizing agent in the process described in Synthesis, December 1995, Pages 1493-1495 gives a yield of 73%. Similarly Pyridinium chlorochromate (PCC) used in WO 2005/077968 gives only 51% yield.

As per WO 2005/077968, the reaction yield obtained for the conversion of compound 2 to compound 4 is 43% only; whereas in Synthesis December 1995, pages 1493-1495, the yield is only 64%.

Chromium (VI) reagents and other reagents derived from dimethyl sulfoxide are commonly used reagents for the oxidation of alcohols to ketones. These reactions require longer reaction times and it is often necessary to use several fold excess of these reagents to obtain a high yield of oxidized product. Workup procedures for chromium (VI) oxidations are more complicated. All chromium (VI) reagents produce solid chromium-containing byproducts, which cannot be removed by extraction, necessitating time-consuming filtration or chromatographic procedure. All chromium containing reagents are, of course toxic and carcinogenic which are not suitable for pharmaceutical preparations.

Thus, there is a need for developing a novel and environmental friendly and better yielding oxidation process at position 6 of the steroid molecule.

Further compound 4 is converted to compound 5 by alkylation in a single step. This direct alkylation results in low yield and produces unwanted 7β epimer. Thus there is a need to provide a better yielding process which reduces the unwanted 7β epimer.

OBJECTS OF THE INVENTION

Figure 1:
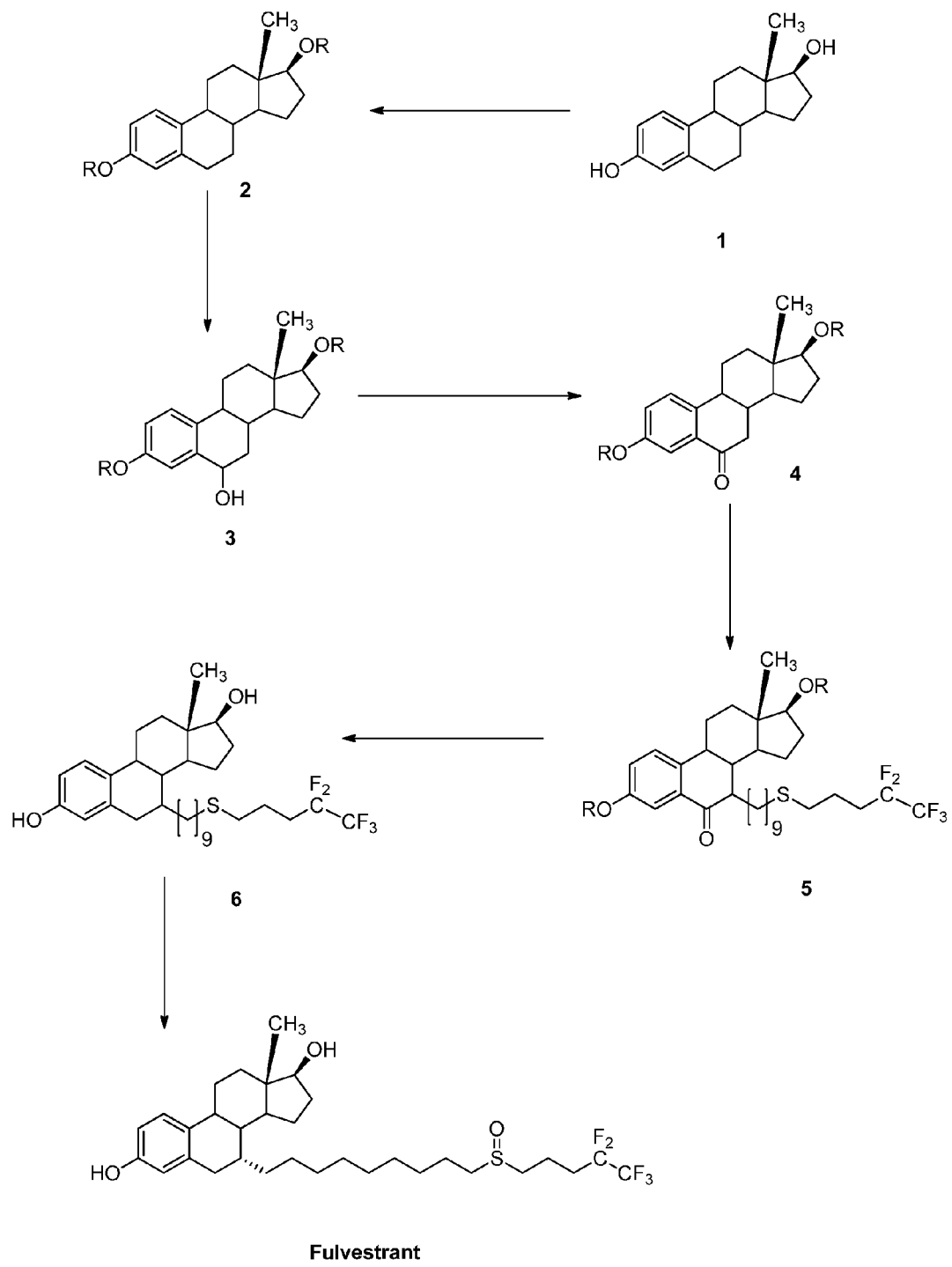
FIG. 1 depicts a general process scheme for the preparation of Fulvestrant.

The main objective of the present invention is to provide environmental friendly and high yield providing process for preparation of Fulvestrant.

In other object of the present invention provides an improved process for preparation of Fulvestrant (I) by oxidizing position 6 of compound of formula FUL-Ia by using Dess-Martin Periodinane (DMP) an oxidizing agent and then adding the side chain in two steps.

In another object provided herein is novel intermediate of Fulvestrant as well as a novel reagent used to extend the side chain and a process for the preparation of the same.

In yet another object of the present invention provides an improved process for preparation of Fulvestrant comprises:
(a) Oxidation of hydroxy group of FUL-Ia by using oxidizing agent Dess-Martin Periodinane to obtain FUL-I
(b) Alkylation of FUL-I with 1,9 dibromononane in a suitable solvent in presence of a base to obtain alkylated derivative of formula FUL-II
(c) Reaction of FUL-II with 4,4,5,5,5-pentafluoropentane phenyl thioester in suitable solvent in presence of a base to obtain the compound of formula FUL-IV
(d) Converting the compound of formula FUL-IV to the Fulvestrant by any conventional methods.

In yet another embodiment of the present invention provides a novel intermediate of compound of formula FUL-II for the preparation of Fulvestrant.

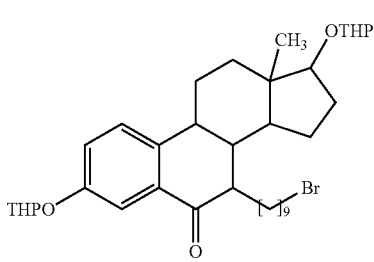

Ful II

SUMMARY OF THE INVENTION

In one aspect of the present invention provides an improved process for preparation of Fulvestrant (I) by oxidizing position 6 of compound of formula FUL-Ia by using Dess-Martin Periodinane (DMP) an oxidizing agent and then adding the side chain in two steps.

In another aspect of the present invention provided herein is novel intermediate of Fulvestrant as well as a novel reagent used to extend the side chain and a process for the preparation of the same.

In yet another aspect of the present invention provides an improved process for preparation of Fulvestrant comprises:
 (a) Oxidation of hydroxy group of FUL-Ia by using oxidizing agent Dess-Martin Periodinane to obtain FUL-I
 (b) Alkylation of FUL-I with 1,9 dibromononane in a suitable solvent in presence of a base to obtain alkylated derivative of formula FUL-II
 (c) Reaction of FUL-II with 4,4,5,5,5-pentafluoropentane phenyl thioester in suitable solvent in presence of a base to obtain the compound of formula FUL-IV
 (d) Converting the compound of formula FUL-IV to the Fulvestrant by any conventional methods.

In yet another aspect of the present invention provide a novel intermediate of compound of formula FUL-II for the preparation of Fulvestrant.

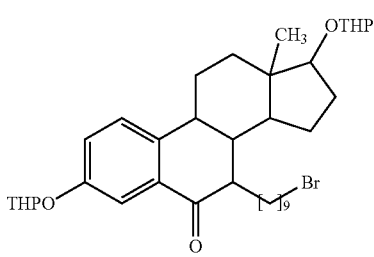

Ful II

DETAILED DESCRIPTION

In one embodiment of the present invention provides an improved process for preparation of Fulvestrant (I) by oxidizing position 6 of compound of formula FUL-Ia by using Dess-Martin Periodinane (DMP) oxidizing agent and then adding the side chain in two steps.

In another embodiment present invention provided herein is novel intermediate of Fulvestrant as well as a novel reagent used to extend the side chain and a process for the preparation of the same.

In yet another embodiment of the present invention provides an improved process for preparation of Fulvestrant comprises:
 (a) Oxidation of hydroxy group of FUL-Ia by using oxidizing agent Dess-Martin Periodinane to obtain FUL-I
 (b) Alkylation of FUL-I with 1,9 dibromononane in a suitable solvent in presence of a base to obtain alkylated derivative of formula FUL-II
 (c) Reaction of FUL-II with 4,4,5,5,5-pentafluoropentane phenyl thioester in suitable solvent in presence of a base to obtain the compound of formula FUL-IV
 (d) Converting the compound of formula. FUL-IV to the Fulvestrant by any conventional methods.

In yet another embodiment of the present invention provide a novel intermediate of compound of formula FUL-II for the preparation of Fulvestrant.

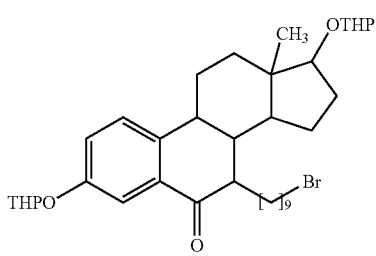

Ful II

The suitable solvent used for both the steps (b) and (c) for alkylation and chain extension are for example chosen from the solvents selected from the water, an aromatic hydrocarbon, e.g., benzene, toluene, xylene, methylbenzene, dimethylbenzene and the like; an alkanol, e.g., methanol, ethanol, 1-butanol, isopropanol and the like; a ketone, e.g., 2-propanone, 4-methyl-2-pentanone, acetone and the like; an ether, e.g., Diethyl ether, dimethyl ether, isopropyl ether, tetrahydrofuran, 1,4-dioxane, 1,1'-oxybisethane and the like; an ether ethyl acetate, methyl acetate and like, a dipolar aprotic solvent, e.g., N,N-dimethylformamide, N,N-dimethylacetamide, dimethyl sulfoxide, nitrobenzene, 1-methyl-2-pyrrolidinone and the like; a halogenated hydrocarbon, e.g. dichloromethane, 1,2-dichloroethane, trichloromethane and the like; a nitrile e.g. acetonitrile, propionitrile and like, carboxylic acids e.g. acetic acid, propanoic acid and like or a mixture of such solvents.

The suitable base used for both the steps (b) and (c) for alkylation and chain extension are for example chosen from an alkali or an earth alkaline metal carbonate, hydrogen carbonate, alkoxide, hydride, amide, hydroxide, acetate or oxide, e.g., sodium carbonate, sodium hydrogen carbonate, potassium carbonate, sodium methoxide, sodium ethoxide, potassium tert, butoxide, sodium hydride, sodium amide, sodium hydroxide, sodium acetate, calcium carbonate, calcium hydroxide, calcium oxide and the like; alkali metal iodide such as sodium iodide, potassium iodide and like or an organic base, such as, for example, an amine, e.g., N,N-diethylethanamine, N,N-(1-methylethyl)-2-propanamine, triethylamine, diethylamine, 4-ethylmorpholine, pyridine, morpholin, piperidine and the like or a mixture of such bases.

The following examples illustrate the present invention and as such are not be considered as limiting the invention set forth in the claims appended hereto.

Example-1

Preparation of Ful-I

To 20.9 g of Ful-Ia in 200 ml of DCM and 10 ml of Pyridine, (5%) at 20° C. was added 21.355 g of DMP, (1.1 eqv) and stirred at RT over 1 h. By this time the reaction is over by TLC and HPLC. Quenched the reaction at 10° C. with 100 ml of 20% Na2SO3 solution and extracted with DCM. The organic phase was washed with 2×H2O and brine. Dried the organic phase over Na2SO4 and taken to dryness to obtain 22 g of crude ketone 3. The crude product was pre-adsorbed over Silica gel, 0.5 ml and loaded on a silica column, column using Hex/Acetone to obtain 19.7 g of pure compound 4 in 95% yield.

Example-1

Preparation of Ful-I

To a solution of Ful-Ib (11.24 gm) in 130.0 ml of toluene was added 0.1 gm picric acid followed by addition of 3.55 ml DHP. The reaction mass was allowed to stir and heated up to reflux temperature (110° C.). The reaction was maintained at reflux until the completion of reaction on TLC. The reaction mass was allowed to cool to room temperature (25-30° C.). The cooled reaction mass was washed with 5% aqueous TEA solution (100 ml) to obtain crude product as oily mass. The obtained crude product was purified by column chromatography to give oily or semi solid product FUL-I (Approx. weight—14 to 15 gm).

Example-2

Preparation of FUL-II

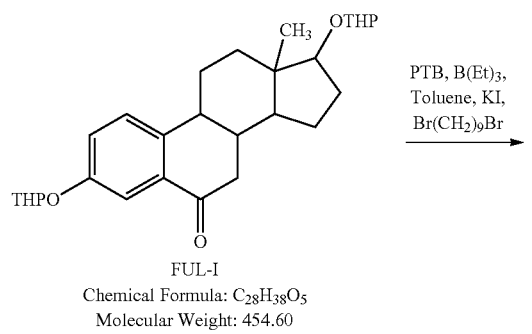

FUL-I
Chemical Formula: $C_{28}H_{38}O_5$
Molecular Weight: 454.60

PTB, B(Et)$_3$,
Toluene, KI,
Br(CH$_2$)$_9$Br

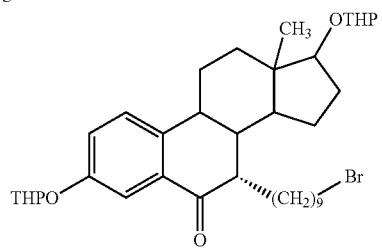

FUL-II
Chemical Formula: $C_{37}H_{55}BrO_5$
Molecular Weight: 659.73

To a solution of 80.0 ml toluene was added FUL-I (8.4 gm) followed by addition of 1.0 M triethylborane in THF solution (18.5 ml) and Potassium tert. Butoxide (PTB) (2.07 gm). The reaction mass was allowed to stir and heated up to reflux temperature (110° C.). The reaction was maintained at reflux for 10 min. Then the heating was removed and potassium iodide (0.3 gm) was added to the reaction mass followed by sequential addition of 1,9-dibromononane (7.55 ml) and Potassium tert. Butoxide (PTB) (2.5 gm). The reaction was maintained at reflux until the completion of reaction on TLC. The reaction mass was allowed to cool to room temperature (25-30° C.). The reaction mass was quenched with 20% aqueous NH$_4$Cl solution (50 ml) to obtain crude product as oily mass. The obtained crude product was purified by column chromatography to give yellow oily mass as FUL-II. (Approx. weight—6 gm)

Example-3

Preparation of FUL-III

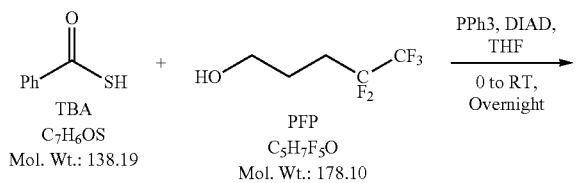

TBA
$C_7H_6OS$
Mol. Wt.: 138.19

PFP
$C_5H_7F_5O$
Mol. Wt.: 178.10

PPh3, DIAD,
THF
0 to RT,
Overnight

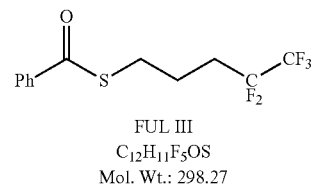

FUL III
$C_{12}H_{11}F_5OS$
Mol. Wt.: 298.27

To a mixture of 104 gm triphenyl phosphine and 78 ml of DIAD charged 55 gm thiobenzoic acid followed by addition of 47 gm pentafluoro pentanol in 25o ml THF at 0° C. slowly in 1 hrs. Raised the temperature up to room temperature and maintain reaction overnight (16 hrs). Confirmed the absence of KSM by TLC. Distilled out solvent from organic layer completely to obtained yellow oily product. (Approx weight 75 gm)

Example-4

Preparation of FUL-IV

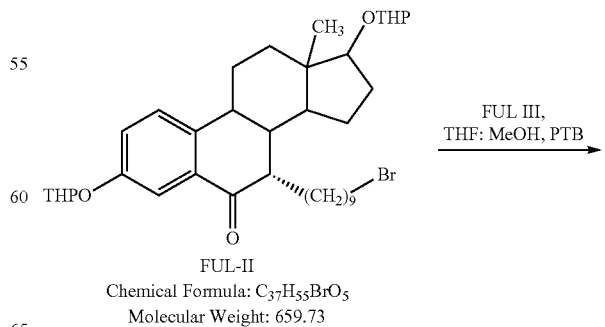

FUL-II
Chemical Formula: $C_{37}H_{55}BrO_5$
Molecular Weight: 659.73

FUL III,
THF: MeOH, PTB

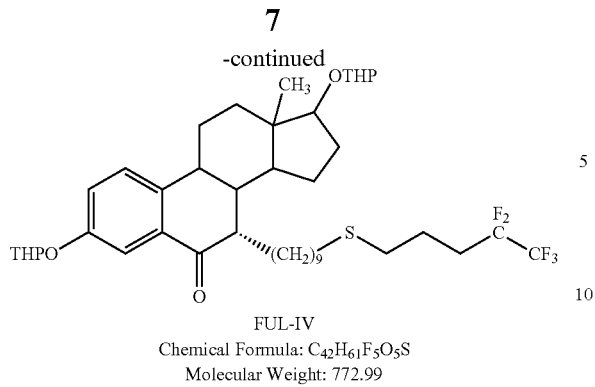

FUL-IV
Chemical Formula: $C_{42}H_{61}F_5O_5S$
Molecular Weight: 772.99

To 80.0 ml of tetrahydrofuran was added FUL-II (8.7 gm) followed by addition of methanol (80.0 ml). Ful-III (3.95 gm) was added to the above reaction mixture followed by Potassium tert. Butoxide (PTB) (1.48 gm). The reaction mass was heated up to 70° C. and maintained at same temperature until the completion of reaction on TLC. The reaction mass was quenched with 20% aqueous $NH_4Cl$ solution (50 ml) to obtain crude product as oily mass (12 to 14 gm). The obtained crude product was purified by column chromatography to give yellow oily mass as, FUL-IV. (Approx. weight—7 gm)

Example-5

Deprotection and Reduction of FUL-IV

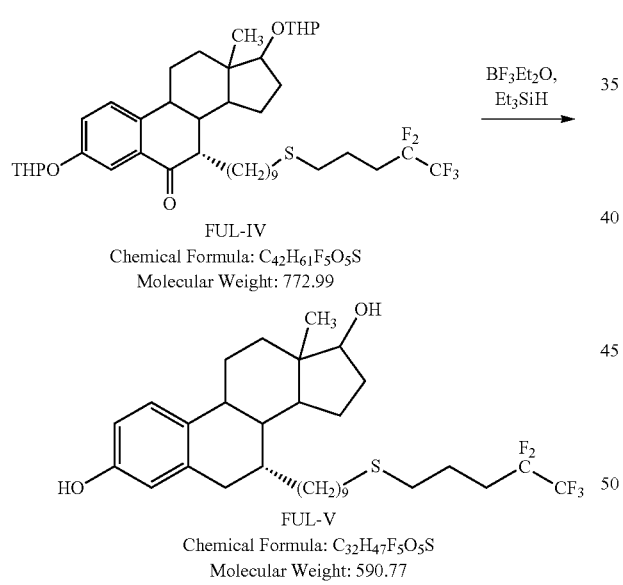

To a mixture of methylene chloride (175 ml) and methanol (175 ml), Ful-IV (9.4 gm) was added followed by addition of Conc. HCl (9.5 ml). Above reaction mass was allowed to maintain for 1 hour and then it was quenched with 10% sodium bicarbonate solution (350 ml). Organic layer from reaction mass was separated and distilled to obtain residues. To the diluted solution of above obtained residues in methylene chloride (350 ml) was added triethylsilane (60 ml) followed by drop wise addition of $BF_3.Et_2O$ (200 ml). The reaction was maintained at reflux for overnight until the completion of reaction on TLC. The reaction mass was cooled to 0° C. temperature. The reaction mass was quenched with ice to obtain crude product (Approx. weight—9 gm). The obtained crude product was purified by column chromatography to give yellow oily mass as FUL-V. (Approx. weight—5.3 gm).

Example-6

Oxidation of FUL-V

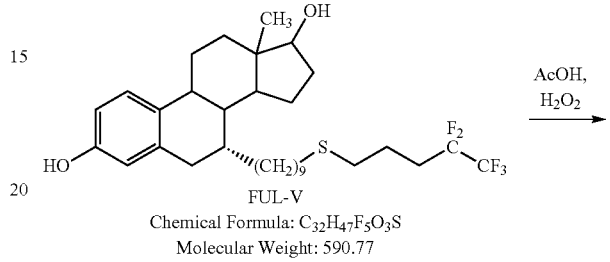

FUL-V
Chemical Formula: $C_{32}H_{47}F_5O_3S$
Molecular Weight: 590.77

FUL-VI (Crude Fulvestrant)
Chemical Formula: $C_{32}H_{47}F_5O_3S$
Molecular Weight: 606.77

To 20.0 ml ethyl acetate was added Ful-V (1.68 gm) followed by addition of acetic acid (1.04 gm) and 785 µl 17% aqueous $H_2O_2$. The reaction was maintained for overnight. The reaction mass was then quenched with ice and the product was extracted with ethyl acetate. The obtained crude product was purified by column chromatography to give yellow oily mass as FUL-VI (Crude fulivastrant) (Approx. weight—1.2 gm).

Example-7

Purification of FULVESTRANT

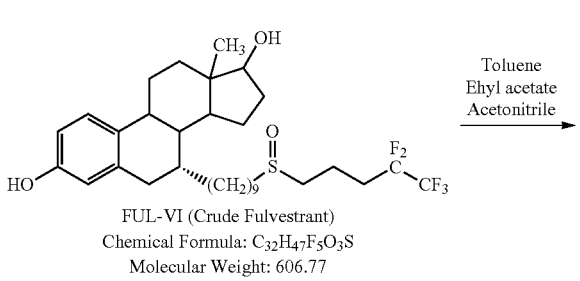

FUL-VI (Crude Fulvestrant)
Chemical Formula: $C_{32}H_{47}F_5O_3S$
Molecular Weight: 606.77

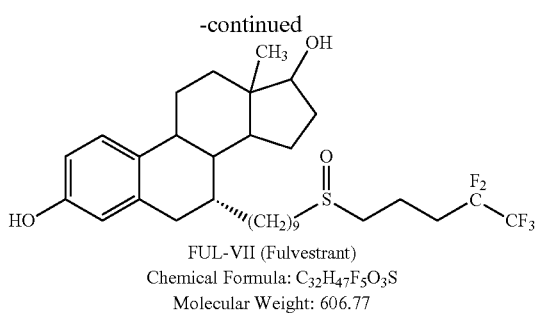

FUL-VII (Fulvestrant)
Chemical Formula: $C_{32}H_{47}F_5O_3S$
Molecular Weight: 606.77

To 200 ml of toluene was added FUL-VI (12.5 gm). The temperature of solution was raised up to 75° C. and maintained for 15 min followed by cooling to room temperature (30±5° C.). The product was filtered and washed with hexane (20.0 ml). (Approx. weight—11±0.5 gm).

To 120 ml of toluene was added above obtained product (11±0.5 gm) followed by addition of ethyl acetate (18.0 ml). The temperature of solution was raised up to 75° C. and maintained for 15 min followed by cooling to room temperature (30±5° C.). The product was filtered and washed with hexane (20.0 ml). (Approx. weight—10±0.5 gm).

To 100 ml of toluene was added above obtained product (10±0.5 gm) followed by addition of acetonitrile (7.0 ml). The temperature of solution was raised up to 75° C. and maintained for 15 min followed by cooling to room temperature (30±5° C.). The product was filtered and washed with hexane (20.0 ml). (Approx. weight—9±0.5 gm).

Figure 2:
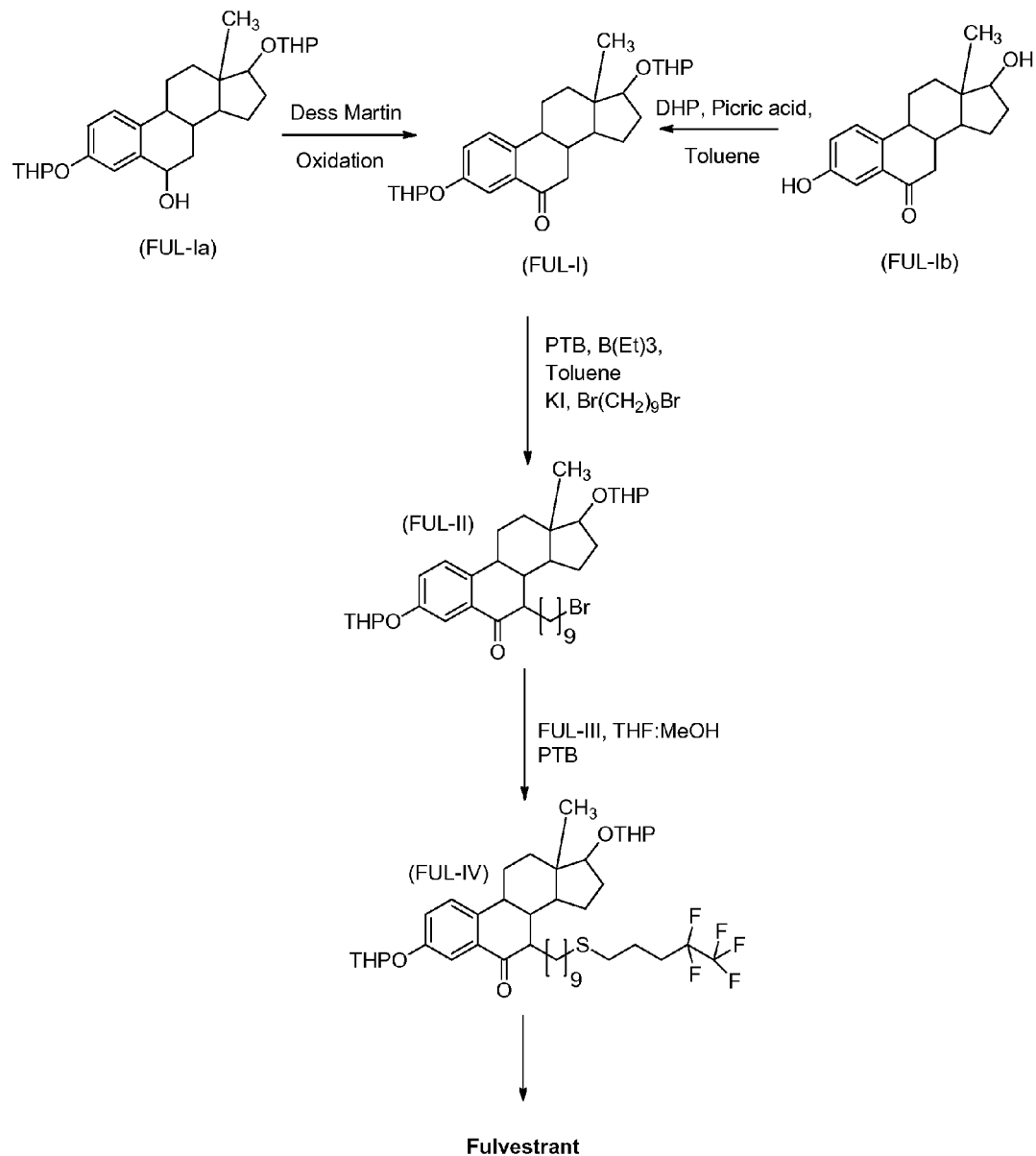
FIG. 2 depicts a reaction scheme illustrated in the Examples.

The process can be depicted by FIG. 2.

We claim:

1. A process for preparing Fulvestrant comprising:
(a) oxidizing the hydroxy group of FUL-Ia

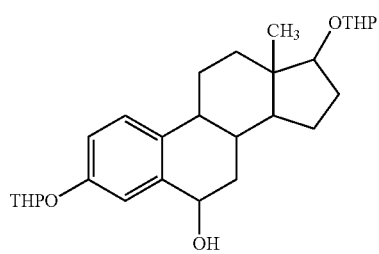

(FUL-Ia)

by using the oxidizing agent Dess-Martin Periodinane to obtain FUL-I

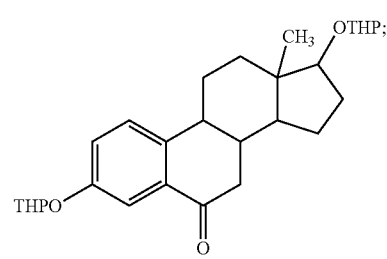

(FUL-I)

(b) alkylating FUL-I with 1,9-dibromononane in a solvent in presence of a base to obtain the alkylated derivative of formula FUL-II

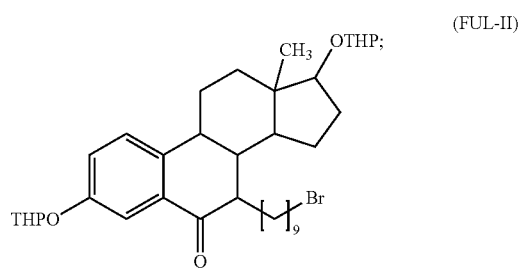

(FUL-II)

(c) reacting FUL-II with 4,4,5,5,5-pentafluoropentane phenyl thioester in a solvent in presence of a base to obtain the compound of formula FUL-IV

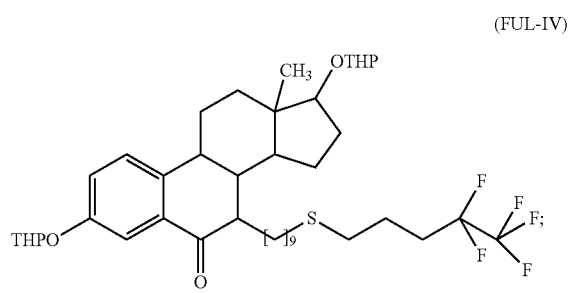

(FUL-IV)

(d) converting the compound of formula FUL-IV to Fulvestrant.

2. The process as claimed in claim 1, wherein the solvent used in both steps (b) and (c) is selected from the group consisting of water, an aromatic hydrocarbon, an alkanol, a ketone, an ether, an ether ethyl acetate, methyl acetate, a dipolar aprotic solvent, a halogenated hydrocarbon, a nitrile, carboxylic acids or a mixture thereof.

3. The process as claimed in claim 1, wherein the base used in both steps (b) and (c) is selected from the group consisting of an alkali or an earth alkaline metal carbonate, hydrogen carbonate, alkoxide, hydride, amide, hydroxide, acetate or oxide, alkali metal iodide, or an organic base, or a mixture thereof.

4. A compound of formula FUL-II,

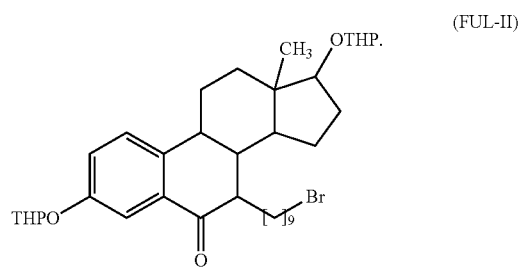

(FUL-II)

5. The method of claim 3, wherein the hydride comprises sodium hydride.

6. The method of claim 2, wherein the aromatic hydrocarbon is selected from the group consisting of benzene, toluene, xylene, methylbenzene, and dimethyl benzene.

7. The method of claim 2, wherein the alkanol is selected from the group consisting of methanol, ethanol, isobutanol, and isopropanol.

8. The method of claim 2, wherein the ketone is selected from the group consisting of 2 propanone, 4-methyl-2-pentanone, and acetone.

9. The method of claim 2, wherein the dipolar aprotic solvent is selected from the group consisting of N,N-dimethylformamide, N,N-dimethylacetamide, dimethyl sulfoxide, nitrobenzene, and 1-methyl-2-pyrrolidinone.

10. The method of claim 2, wherein the halogenated hydrocarbon is selected from the group consisting of dichloromethane, 1,2-dichloroethane, and trichloromethane.

11. The method of claim 2, wherein the carboxylic acids is selected from the group consisting of acetic acid, and propanoic acid.

12. The method of claim 2, wherein the ether is selected from the group consisting of diethyl ether, dimethyl ether, isopropyl ether, tetrahydrofuran, and 1,4-dioxane.

13. The method of claim 3, wherein the alkali carbonate or alkali hydrogen carbonate is selected from the group consisting of sodium carbonate, sodium hydrogen carbonate, potassium carbonate, and calcium carbonate.

14. The method of claim 3, wherein the alkoxide is selected from the group consisting of sodium methoxide, sodium ethoxide, and potassium tertbutoxide.

15. The method of claim 3, wherein the alkali metal iodide is selected from the group consisting of sodium iodide, and potassium iodide.

16. The method of claim 3, wherein the organic base is selected from the group consisting of N,N-dimethylehtanamine, N,N-(1-methylethyl)-2-propanamine, trimethylamine, diethylamine, 4-ethylmorpholine, pyridine, morpholin, and piperidine.

17. The method of claim 3, wherein the hydroxide comprises sodium hydroxide and calcium hydroxide.

* * * * *